(12) United States Patent
Pollak et al.

(10) Patent No.: US 12,178,542 B2
(45) Date of Patent: Dec. 31, 2024

(54) TEMPORARY PACEMAKER SYSTEMS AND DEPLOYMENT SYSTEMS

(71) Applicant: Mayo Foundation for Medical Education and Research, Rochester, MN (US)

(72) Inventors: Peter M. Pollak, Atlantic Beach, FL (US); Samuel J. Asirvatham, Rochester, MN (US); Charles J. Bruce, Ponte Vedra Beach, FL (US); Paul A. Friedman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/431,542

(22) Filed: Feb. 2, 2024

(65) Prior Publication Data
US 2024/0173093 A1  May 30, 2024

Related U.S. Application Data

(62) Division of application No. 16/971,373, filed as application No. PCT/US2019/019813 on Feb. 27, 2019, now Pat. No. 11,903,670.

(60) Provisional application No. 62/635,842, filed on Feb. 27, 2018.

(51) Int. Cl.
| | |
|---|---|
| *A61B 5/06* | (2006.01) |
| *A61B 46/00* | (2016.01) |
| *A61B 46/10* | (2016.01) |
| *A61B 46/20* | (2016.01) |

(52) U.S. Cl.
CPC .............. *A61B 46/20* (2016.02); *A61B 5/062* (2013.01); *A61B 46/10* (2016.02); *A61B 46/40* (2016.02)

(58) Field of Classification Search
CPC ......... A61B 46/10; A61B 46/20; A61B 46/40; A61B 5/062
See application file for complete search history.

(56) References Cited

U.S. PATENT DOCUMENTS

| | | | | |
|---|---|---|---|---|
| 4,162,679 | A * | 7/1979 | Reenstierna | A61N 1/0565 607/122 |
| 4,214,594 | A * | 7/1980 | Little | A61N 1/056 607/122 |
| 6,173,206 | B1 * | 1/2001 | Shchervinsky | A61N 1/0587 607/132 |
| 8,489,205 | B2 * | 7/2013 | Stotts | A61N 1/37205 607/130 |
| 8,527,068 | B2 * | 9/2013 | Ostroff | A61N 1/37518 607/119 |
| 8,639,357 | B2 * | 1/2014 | Tomaschko | A61M 25/0082 607/122 |
| 9,216,280 | B1 * | 12/2015 | Hakki | A61N 1/05 |
| 2003/0065373 | A1 * | 4/2003 | Lovett | A61N 1/05 607/122 |
| 2006/0241733 | A1 * | 10/2006 | Zhang | A61N 1/056 607/122 |

(Continued)

*Primary Examiner* — Camtu T Nguyen
(74) *Attorney, Agent, or Firm* — Fish & Richardson P.C.

(57) ABSTRACT

Devices and methods for the treatment of heart conditions, and other medical purposes, include cardiac pacing systems. For example, this document describes temporary transvenous endocardial pacemaker systems and devices for deploying such systems without the need for conventional imaging procedures.

7 Claims, 2 Drawing Sheets

(56) References Cited

U.S. PATENT DOCUMENTS

| | | | |
|---|---|---|---|
| 2007/0208402 A1* | 9/2007 | Helland | A61N 1/056 607/119 |
| 2012/0109149 A1* | 5/2012 | Bonner | A61N 1/372 606/129 |
| 2012/0185023 A1* | 7/2012 | Clark | A61N 1/059 29/874 |
| 2012/0220854 A1* | 8/2012 | Messerly | A61B 5/742 600/409 |
| 2014/0130810 A1* | 5/2014 | Azizian | A61B 46/10 128/849 |
| 2015/0018907 A1* | 1/2015 | Razavi | A61B 34/20 607/116 |
| 2016/0100892 A1* | 4/2016 | Wu | A61B 46/00 128/853 |
| 2016/0331461 A1* | 11/2016 | Cheatham, III | A61B 46/10 |

* cited by examiner

TEMPORARY PACEMAKER SYSTEMS AND DEPLOYMENT SYSTEMS

CROSS-REFERENCE TO RELATED APPLICATIONS

This application is a divisional application of U.S. patent application Ser. No. 16/971,373 filed on Aug. 20, 2020, which is a National Stage application under 35 U.S.C. § 371 of International Application No. PCT/US2019/019813 having an International Filing Date of Feb. 27, 2019, which claims priority to U.S. Patent Application Ser. No. 62/635,842, filed on Feb. 27, 2018. The disclosure of the prior applications are considered part of the disclosure of this application, and are incorporated in its entirety into this application.

BACKGROUND

1. Technical Field

This document relates to devices and methods for the treatment of heart conditions and for other medical purposes. For example, this document relates to temporary transvenous endocardial pacemaker systems and devices for deploying such systems without the need for conventional imaging procedures.

2. Background Information

A variety of health conditions can prompt the need for a patient to have temporary cardiac pacing support. For example, patients that undergo heart valve surgery may experience a need for temporary pacing. Age-related degeneration of the patient's conduction system, and other metabolic conditions can also contribute to the need for temporary pacing. Some patients may have a transient cause of bradyarrhythmia such as electrolyte abnormalities or medication overdose.

For treatment, as part of advanced cardiac life support algorithms, patients are sometimes given atropine, which is generally ineffective for both transplanted hearts or in conduction disturbances below the Bundle of His. Another treatment commonly given is a chronotropic agent such as dopamine or epinephrine.

If these medications fail to provide an adequate remedy, then transcutaneous pacing may be tried. Transcutaneous pacing is most commonly delivered by defibrillator pads applied to "anterior/posterior" or "right chest/left axilla" locations of the patients. The defibrillator is then able to pace the patient's heart using high energy in its pacing mode. This pacing may be uncomfortable and/or painful for many patients, as it results in skeletal muscle contractions synchronous with the pacing. The effectiveness of the pacing is limited by contact of the defibrillator pads with the skin (such as by hair), larger body habitus, and COPD which limit the current delivery to the heart.

If transcutaneous pacing fails to provide an adequate remedy, then transvenous pacing may be tried. Placement of a temporary pacemaker wire transvenously may require placement of a central line under fluoroscopy (with the requisite leaded apron protection and additional personnel such a radiology tech). Depending on the type of temporary pacemaker placed, there may be barriers to the placement, including technical expertise to achieve the placement. The transvenous pacing lead may become dislodged after completion of the placement procedure, and this requires additional fluoroscopy to reposition the transvenous lead.

SUMMARY

This document describes devices and methods for the treatment of heart conditions and for other medical purposes. For example, this document describes temporary transvenous endocardial pacemaker systems and devices for deploying such systems without the need for conventional imaging procedures.

Transcutaneous pacing tends to be uncomfortable and painful for patients. Transvenous temporary pacing is a preferred option, but currently requires central access under imaging. One aspect of the invention described herein provides an efficient way for deploying a temporary transvenous pacing system.

In one aspect, this disclosure is directed to a patient drape device, that includes a flexible substrate configured to cover a portion of a patient, and a plurality of indicator lights attached to the flexible substrate. Each of the indicator lights actuates to a lit condition in response to a magnetic field or radiofrequency (RF) emanating from within the patient, or in response to another type of detection modality as described further herein.

Such a patient drape device may optionally include one or more of the following features. The patient drape may also include one or more electromagnets attached to the flexible substrate. The flexible substrate may include one or more shapes or markings to align the patient drape device to the patient's body. The flexible substrate may be configured to cover a chest of the patient. Each of the indicator lights may be individually selectively de-activated. Each of the indicator lights may actuate to two or more types of lit conditions. The two or more types of lit conditions may comprise different colors of light. The two or more types of lit conditions may comprise different intensities of light.

In another aspect, this disclosure is directed to a temporary transvenous pacemaker system that includes a pulse generator, an electrode wire coupleable to the pulse generator and including a bi-polar electrode pair at a distal tip of the electrode, and a patient drape device. The patient drape device includes a flexible substrate configured to cover a portion of a patient, and a plurality of indicator lights attached to the flexible substrate. Each of the indicator lights actuates to a lit condition in response to a magnetic field emanating from the distal tip. The bi-polar electrode pair is configured to transmit electrical pulses from the pulse generator to tissue contacting the bi-polar electrode pair.

Such a temporary transvenous pacemaker system may optionally include one or more of the following features. The distal tip may include an electromagnet that generates the magnetic field. In some embodiments, the distal tip may include a radiofrequency (RF) generator. The pulse generator may be configured to be used external to the patient. The patient drape may also include one or more electromagnets or RF antennas attached to the flexible substrate. In some cases, the one or more electromagnets can be used to influence the positioning of the distal tip. The distal tip may be selectively expandable. The distal tip may include anchor elements to engage with the tissue. The anchor elements may be bioabsorbable.

In another aspect, this disclosure is directed to a method for temporarily pacing a heart of a patient. The method includes (i) percutaneously navigating an electrode wire within the patient's vasculature; (ii) tracking, during the navigating, locations of a distal tip of the electrode wire using a patient drape device in contact with a portion of the patient, wherein the patient drape device includes a plurality of indicator lights attached to a flexible substrate, wherein the tracking comprises lighting one or more of the indicator lights responsive to a magnetic field emanating from the distal tip; (iii) positioning the distal tip in contact with endocardial tissue of the patient; and (iv) delivering pulses from the distal tip to the endocardial tissue.

Such a method may optionally include one or more of the following features. The method may also include activating one or more electromagnets attached to the flexible substrate to steer the distal tip within the vasculature. A portion of the electrode wire may reside within a brachial artery of the patient. The method may be performed without the use of fluoroscopy. The method may also include, after the positioning the distal tip in contact with the endocardial tissue of the patient, expanding the distal tip and anchoring the distal tip to the endocardial tissue.

Particular embodiments of the subject matter described in this document can be implemented to realize one or more of the following advantages. First, in accordance with some embodiments described herein patients with a need for temporary pacing support (e.g., for time periods of about one day to about three months) can be treated by a central access pacing system that is readily installable. For example, in some such cases, the need to use x-ray fluoroscopy during the placement of the pacing system is advantageously negated. Accordingly, patients and providers experience less exposure to x-rays. Additionally, in some cases the placement of the pacing system can take place in the hospital bed, ambulance, field, etc., where fluoroscopy systems are unavailable or inconvenient. Moreover, the devices and systems provided herein are designed to assist clinicians during the process of installing temporary pacing support systems. In result, the installation process may, in some cases, be able to be performed by a broader range of clinicians (e.g., experiences, skill sets, training backgrounds, etc.). The devices and systems described herein can be used to advantageously reduce recovery times, patient discomfort, and treatment costs. The devices and systems described herein can be adapted to other uses such as, but not limited to, the installation of peripherally inserted central catheter ("PICC") lines, chest tubes, peritoneal drains, other catheters or devices of various types, and the like.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices and methods for the treatment of heart conditions. For example, this document describes temporary transvenous endocardial pacemaker systems and devices for deploying such systems without the need for conventional imaging procedures.

Figure 1:
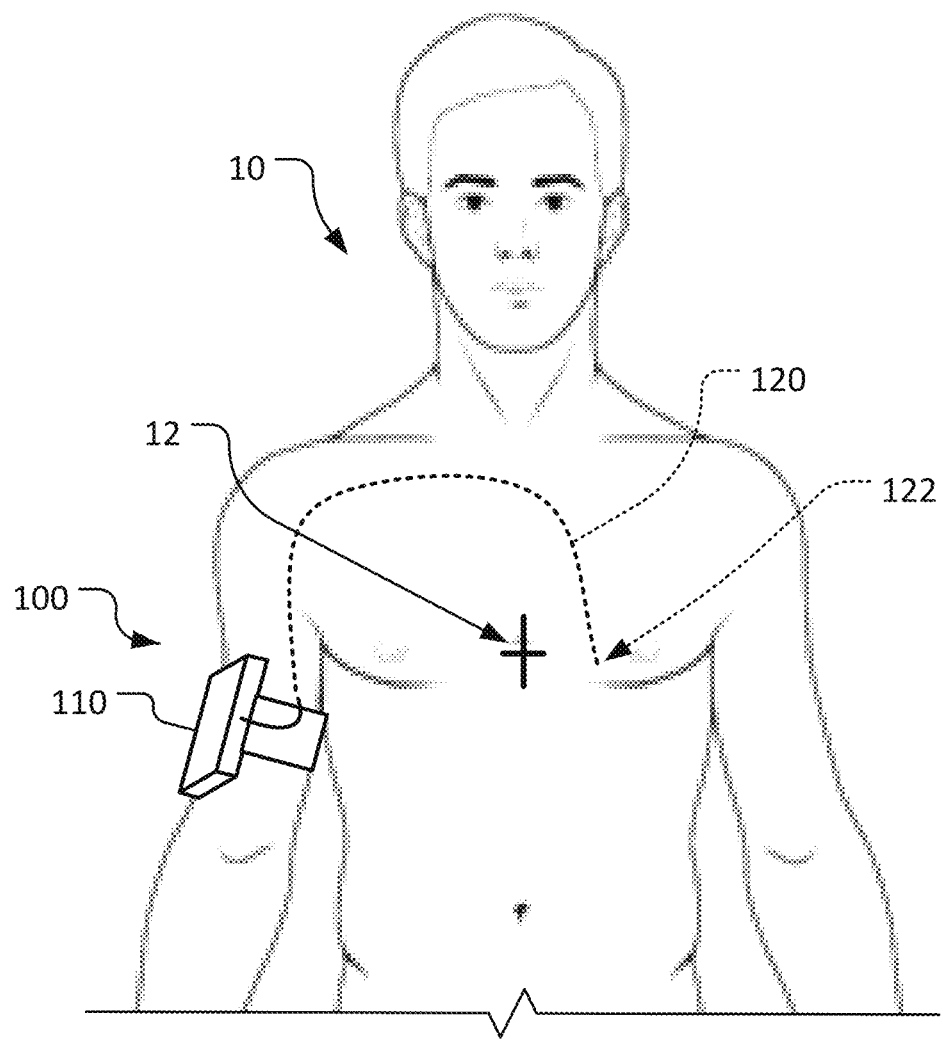
FIG. 1 is an anterior view of a patient that is being treated using a temporary central access pacemaker system in accordance with some embodiments provided herein.

Referring to FIG. 1, a patient 10 is shown being treated by an example transvenous temporary endocardial pacemaker system 100 in accordance with some embodiments. In the depicted embodiment, transvenous temporary endocardial pacemaker system 100 includes a generator 110 and a transvenous pacing lead 120. Transvenous temporary endocardial pacemaker system 100 can provide pacing to the heart of patient 10 to treat arrhythmias. A tip 122 of transvenous pacing lead 120 can includes one or more electrodes (e.g., bipolar electrode pairs or one or more unipolar electrodes) that reside in contact with endocardial tissue (e.g., in the right ventricle). Transvenous pacing lead 120 can be designed for temporary use (e.g., for time periods of about one day to about three months).

The depicted arrangement utilizes venous access via a brachial artery of patient 10. In some cases, other venous access pathways can be used, such as, but not limited to, transjugular and transfemoral. The transbrachial access as depicted can provide mobility advantages in comparison to other venous access pathways.

Generator 110 (e.g., external automatic cardioverter defibrillator) can be equipped for short-range wireless communications with monitoring equipment to enhance mobility of patient 10. Generator 110 can be re-chargeable and re-useable.

In addition to electrodes, tip 122 of transvenous pacing lead 120 can include one or more anchoring and/or anti-migration features. Such anchoring and/or anti-migration features can be active or passive anchoring features, or a combination of both active and passive. For example, in some cases tip 122 can include one or more selectively deployable screws (e.g., spiral tines), hooks, barbs, or tines that are actively engageable with endocardial tissue. In some cases, tip 122 can include one or more tines that are passively engageable with endocardial tissue (e.g., like a grappling hook arrangement). In some cases, tip 122 is selectively expandable such that the electrodes and the anchoring and/or anti-migration features engage with tissue at the time of expansion of tip 122.

In some cases, the anchoring and/or anti-migration features (or portions thereof) of tip 122 are bioabsorbable (e.g., made of a dissolving polymer). The bioabsorbable aspect can facilitate retrieval of temporary transvenous pacing lead 120. In some cases, the anchoring and/or anti-migration features (or portions thereof) of tip 122 are electro-phasic polymer passive fixation tines that release when appropriate electrical energy is applied. Differing types of anchoring and/or anti-migration features can be used depending on the anticipated length of use (time period) of a particular temporary transvenous pacing lead 120.

In some implementations, tip 122 includes one or more features for visualizing or guiding tip 122 during the deployment process. For example, in some cases tip 122 includes one or more magnetic elements (e.g., electromagnets). Such magnetic elements can be used to facilitate guidance of temporary transvenous pacing lead 120 during transvenous deployment, as described further below. In some cases, tip 122 can include an ultrasound emitter/marker for use with ultrasound guidance during the deployment process.

In some implementations, tip 122 includes an impedance sensor, flow sensor, pressure sensor, or combinations thereof to provide an indication of when tip 122 is against an endocardial tissue surface. Moreover, in some implementations the electrodes of tip 122 can provide electrogram-based information that can be used for this purpose.

In some cases, transvenous pacing lead 120 can be installed over a previously-placed guidewire. In some such cases, the guidewire can be installed using ultrasound (e.g., a hand-held device) for visualization.

Figure 2:
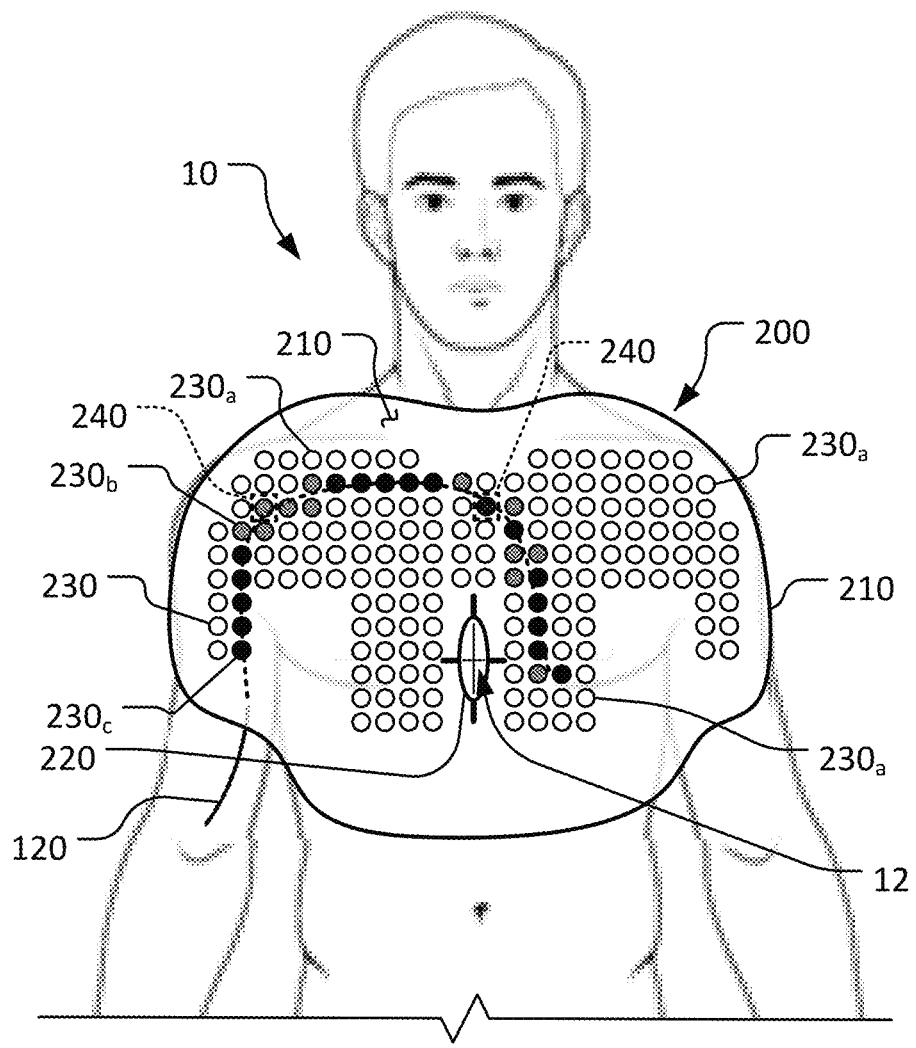
FIG. 2 shows the installation of the temporary central access pacemaker system of FIG. 1 using an example drape device covering the chest of the patient.

Referring also to FIG. 2, in some implementations a drape device 200 temporarily covering the chest of patient 10 can be used to facilitate the navigation and installation of transvenous devices. In the depicted example, temporary transvenous pacing lead 120 is being transvenously navigated and installed using drape device 200. In other implementations, drape device 200 can be adapted for use in conjunction with the installation of other medical devices such as, but not limited to, PICC lines, chest tubes, peritoneal drains, other devices or catheters of various types, and the like. While in the depicted implementation drape device 200 is shown on the thoracic region of patient 10, it should be understood that drape device 200 can be adapted for use on other anatomical portions of patient 10. In general, drape device 200 includes a flexible substrate 210 to which multiple indicator lights $230_{a-c}$ and one or more magnetic devices 240 (optional) are coupled. In some cases, drape device 200 is re-usable (e.g., by having a disposable liner that interfaces with patient 10, or by being sterilize-able). In some cases, drape device 200 is a single-use device. While in the depicted embodiment drape device 200 covers the chest of patient 10, in some embodiments drape device 200 can be designed and used to cover other portions of patient 10 (e.g., for femoral access, for use with PICC lines, etc.). In some embodiments, two or more drape devices 200 can be used on patient 10 to facilitate a transvenous installation of one or more wires, leads, catheters, and the like.

Flexible substrate 210 can include one or more features, such as fiduciary markers, by which drape device 200 is properly align-able with patient 10 (and repeatably realign-able in substantially the same orientation on patient 10). Such a feature may be useful to, for example, repeatedly deliver drug treatment to a tumor. In the depicted embodiment, flexible substrate 210 device defines an aperture 220. Aperture 200 can be, for example, aligned with a mark 12 made on the sternum of patient 10 in preparation for using drape device 200. Other types of features for aligning drape device 200 to patient 10 can be additionally or alternatively included (e.g., transparent portions, markings, images, measurement scales/indices, etc.).

Attached to flexible substrate 210 are multiple indicator lights $230_{a-c}$. Indicator lights $230_{a-c}$ can, for example, indicate the location of temporary transvenous pacing lead 120 (e.g., of tip 122 in particular) within patient 10.

In the depicted example, indicator light $230_a$ is an inactivated light, indicator light $230_b$ is an activated light at a first status, and indicator light $230_c$ is an activated light at a second status. The activated lights $230_b$ and $230_c$ indicate the path and/or position of temporary transvenous pacing lead 120 (e.g., of tip 122 in particular). While indicator lights $230_{a-c}$ are described above as having two statuses, in some cases indicator lights 230a-c can have many more statuses based on variances in color, intensity, flashing rate, and so on, and combinations thereof.

In some examples, indicator light $230_b$ that is activated at the first status represents that temporary transvenous pacing lead 120 is (or was) nearby, but not directly under the location of indicator light $230_b$. In some examples, indicator light $230_c$ that is activated light at the second status represents that temporary transvenous pacing lead 120 is (or was) directly under the location of indicator light $230_c$. In some cases, the indicator lights $230_{a-c}$ can be activated using different colors or intensities of light to indicate and differentiate the first and second statuses. In some cases, individual lights of indicator lights $230_{a-c}$ can be selectively deactivated (e.g., cleared after being lit). In some cases, the intensity of indicator lights $230_{a-c}$ can gradually reduce (e.g., slowly fade) after the position of temporary transvenous pacing lead 120 (e.g., of tip 122 in particular) has been detected and then undetected. This can create a "tail" effect (e.g., similar to the concept of a tail of a comet).

As described above, in some cases tip 122 can include an electromagnetic element. Such an electromagnetic element can be used (when activated) by indicator lights $230_{a-c}$ to track the position of tip 122.

In some cases, other position detection techniques besides electromagnetism can be used such that drape 200 can track the position of internal medical devices (such as, but not limited to, temporary transvenous pacing lead 120). For example, in some cases RF can be used. That is, one or more RF generators can be installed on the internal medical device (e.g., at the distal end portion and/or at one or more other locations along the device). In some such embodiments, drape 200 can include a plurality of RF receivers in discrete local areas that are each connected to a respective indicator light. For example, drape 200 can include a plurality of paired RF antenna arrays that are arranged orthogonally. In some embodiments, a control system of drape 200 can use a triangulation technique based on outputs from the paired RF antenna arrays to ascertain an accurate location of the RF emitter on the device (e.g., including indications of the depth of the device in relation to drape 200, including in three dimensional space). In another example, near field communication (NFC) technology can be used. In additional examples, capacitive sensors, metal detectors (e.g., using inductor coils), Hall effect sensors, and the like can be used. In some embodiments, a combination of differing position detection modalities can be used.

In some cases, a desired path for tip 122 can be marked (temporarily or permanently) on substrate 210. Then, the clinician installing temporary transvenous pacing lead 120 can confirm that the desired path is followed (as indicated by the change of indicator lights $230_a$ to activated lights $230_b$ and $230_c$).

In some cases, one or more images of the internal anatomy of patient 10 can be printed or overlaid on drape 200. For example, one or more images from a CT scan, x-ray, or ultrasound can be incorporated onto substrate 210 (or as a separate overlay-able sheet).

In some embodiments, drape 200 can include ultrasound sensitive material to allow localization of internal organs/structures with ultrasound imaging, which can then be used in combination with the detection of a medical device's internal location using indicator lights $230_{a-c}$ as described above. Additionally, or alternatively, in some cases drape 200 is fluoroscopically visible, allowing localization of internal organs/structures to be used in combination with the detection of a medical device's internal location using indicator lights $230_{a-c}$ as described above.

In some implementations, flexible substrate 210 can include one or more selectively actuatable magnetic devices 240. Such magnetic devices 240 may be coupled to flexible substrate 210 at position where tip 122 may need to be deflected, pulled, or steered to follow a desired intravenous path (or to avoid an undesired path). Accordingly, magnetic devices 240 can be selectively activated and can interact with an electromagnetic element on tip 122.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A temporary transvenous pacemaker system, comprising:
    a pulse generator;
    an electrode wire coupleable to the pulse generator and including a bi-polar electrode pair at a distal tip of the electrode, the bi-polar electrode pair configured to transmit electrical pulses from the pulse generator to tissue contacting the bi-polar electrode pair; and
    a patient drape device comprising:
        a flexible substrate configured to cover a portion of a patient; and
        a plurality of indicator lights attached to the flexible substrate, wherein each of the indicator lights actuates to two or more types of lit conditions in response to a magnetic field emanating from the distal tip, and wherein each of the plurality indicator lights can be individually selectively de-activated.

2. The temporary transvenous pacemaker system of claim 1, wherein the distal tip includes an electromagnet configured to generate the magnetic field.

3. The temporary transvenous pacemaker system of claim 1, wherein the pulse generator is configured to be used external to the patient.

4. The temporary transvenous pacemaker system of claim 1, wherein the patient drape further comprises one or more electromagnets attached to the flexible substrate, wherein the one or more electromagnets can influence the positioning of the distal tip.

5. The temporary transvenous pacemaker system of claim 1, wherein the distal tip is selectively expandable.

6. The temporary transvenous pacemaker system of claim 1, wherein the distal tip includes anchor elements configured to engage with the tissue.

7. The temporary transvenous pacemaker system of claim 6, wherein the anchor elements are bioabsorbable.

* * * * *